US006922457B2

United States Patent
Nagata et al.

(10) Patent No.: US 6,922,457 B2
(45) Date of Patent: Jul. 26, 2005

(54) COMPUTER TOMOGRAPHY APPARATUS

(75) Inventors: Kiyoshi Nagata, Tochigi-ken (JP); Masaharu Tsuyuki, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 180 days.

(21) Appl. No.: 10/306,225

(22) Filed: Nov. 29, 2002

(65) Prior Publication Data

US 2003/0099323 A1 May 29, 2003

(30) Foreign Application Priority Data

Nov. 29, 2001 (JP) .................................... P2001-363623

(51) Int. Cl.[7] ............................................. A61B 6/00
(52) U.S. Cl. .............................. 378/19; 378/4; 378/901; 378/15
(58) Field of Search ........................... 378/15, 19, 147, 378/4, 9, 901, 150, 14

(56) References Cited

U.S. PATENT DOCUMENTS

| 5,825,842 | A | | 10/1998 | Taguchi |
| 6,157,696 | A | | 12/2000 | Saito et al. |
| 6,295,331 | B1 | * | 9/2001 | Hsieh ........................... 378/19 |
| 6,529,576 | B2 | * | 3/2003 | Hsieh et al. ................... 378/15 |
| 6,658,082 | B2 | * | 12/2003 | Okumura et al. ............. 378/19 |

FOREIGN PATENT DOCUMENTS

JP          9-192126        7/1997

OTHER PUBLICATIONS

Dennis L. Parker, Technical Notes, Optimal short scan convolution reconstruction for fanbeam CT, Med. Phys. 9(2), Mar./Apr. 1982, pp. 254–257.

L. A. Feldkamp et al., 1984 Optical Society of America, "Practical cone–beam algorithm", J. Opt. Soc. Am. A/vo;l. 1, No. 6/Jun. 1984, pp. 612–619.

* cited by examiner

*Primary Examiner*—Edward J. Glick
*Assistant Examiner*—Elizabeth Keaney
(74) *Attorney, Agent, or Firm*—Oblon, Spivak, McClelland, Maier & Neustadt, P.C.

(57) ABSTRACT

A computer tomography apparatus of this invention includes an x-ray tube configured to emit x-rays while rotating around an object to be examined, a radiation detector configured to have detection elements arranged in a plurality of rows along a slice-thickness direction, each row having a plurality of the detection elements configure to detect x-rays that had passed through the object, a data acquisition system configured to acquire projection data of the object using the output of the radiation detector, and a reconstructing unit configured to be capable of a first reconstruction method and a second reconstruction method, reconstruct an image based on the projection data using one of the first and second reconstruction method, wherein the x-rays are assumed to intersect perpendicularly with an axis of rotation of the x-ray tube in the first reconstruction method, and the second reconstruction method reconstructs the image using a cone angle information of the x-rays.

15 Claims, 4 Drawing Sheets

COMPUTER TOMOGRAPHY APPARATUS

CROSS-REFERENCE TO RELATED APPLICATIONS

This application is based upon and claims the benefit of priority from the prior Japanese Patent Application No. 2001-363623, filed Nov. 29, 2001, the entire contents of which are incorporated herein by reference.

BACKGROUND OF THE INVENTION

1. Field of the Invention

The present invention is directed to an X-ray computer tomography apparatus (i.e., X-ray CT apparatus) configured to scan using multiple row detection in which a plurality of detector elements are arrayed along a central axis direction of subject identified as the slices thickness direction.

2. Description of the Related Art

Conventional x-ray CT devices are single slice devices. A single slice x-ray CT apparatus has an x-ray source and a detector arranged at both sides of an object (for example, a patient). The detector includes about 1000 channels arranged in an arc shape along a direction perpendicular to a body axis (the channel direction).

In a single slice x-ray CT apparatus the x-ray source emits x-ray beams in a fan shape corresponding to a slice of the object to be examined. The detector detects the x-ray beams passes through the slice plane of the object. The acquired X-ray transmission data is sent to a data acquisition system (DAS) having a plurality of data acquisition elements corresponding to x-ray detector elements. The X-ray transmission data is amplified by each of the acquisition elements and projection data is acquired. Data at a predetermined rotation angle is called one view.

The conventional, single-slice x-ray CT apparatus repeats the data acquisition process about 1,000 times per rotation, emitting x-rays while the x-ray source and the detector rotate together around the object to be examined. Thus, the conventional x-ray CT apparatus acquires multidirectional projection data of the object to be examined and reconstructs an image of the slice plane based on the acquired multidirectional projection data.

The conventional x-ray CT apparatus is limited in its ability to scan a wide area in a short time because it only acquires a single image of a plane.

To address this limitation, multi-slice x-ray CT devices have been developed in recent years. The detector of the multi-slice x-ray CT apparatus is a multiple row detector (two-dimensional detector). The multiple row detector comprises detector elements arranged in M channels of N segments. The multi-slice x-ray CT has an x-ray source that emits fan shaped x-ray beams. In addition, the multi-slice CT acquires projection data of a plurality of slice planes simultaneously by emitting cone shaped x-ray beams and then detecting the x-rays passed through the object with the two-dimensional detector. Thus, the multi-slice x-ray CT can scan the wider area than the single slice x-ray CT.

The typical multi-slice x-ray CT apparatus includes a 4 slice type multi-slice CT. Recently, demand has risen for x-ray CT devices with a larger number of detector rows (e.g., 8 slice or 16 slice) that can produce wider area images. However, technical challenges are associated with building devices with larger numbers of detector rows.

The multi-slice x-ray CT apparatus emits fan shaped x-ray beams having a width spread in the direction of the body axis (in other words, a cone shaped x-ray beam). The multi-slice x-ray CT apparatus reconstructs a slice image using a fan-beam reconstruction method in which x-ray beams are assumed to intersect perpendicularly with the rotation center axis of the x-ray source.

However, if the number of the detector rows increases beyond 4, the x-ray beam emitted to the two-dimensional detector can not be assumed to intersect perpendicularly with the rotation center axis (especially, at the end of detector rows). This is because the x-ray beams are assumed to intersect perpendicularly with the rotation axis and a plurality of images as the multiple slices are then reconstructed, the images would generate artifacts which could lead to faulty images which may prevent their use in diagnosis.

In response to these limitations industry has sought an effective and practical method for cone-beam x-ray CT. A cone-beam x-ray CT apparatus can acquire a wider range of data more quickly than the multi-slice x-ray CT apparatus. Thus, it can shorten the scanning time. But, because the cone-beam x-ray CT apparatus needs to reconstruct an image by taking the cone angle into consideration, when many images of the thick slice thickness are reconstructed simultaneously the reconstruction time could become so long as to be limited by processing time.

Also, in order to acquire the data using a plurality of rows detector (for example, 32 rows and 64 rows), the number of data acquisition systems (DAS) must correspond to the number of rows of the detection element rows. However there is a limitation in the number of DAS elements that can be used due to limited mounting space in a system (gantry), cost, performance, and other considerations.

Japanese Patent Publication (KOKAI) NO. 9-192126, the entire contents of which are hereby incorporated by reference, discloses an x-ray CT apparatus which selects fan-beam reconstruction or cone-beam reconstruction according to the slice position to be reconstructed. However, the image quality (noise level) of each slice is not constant when reconstructing a plurality of slices in a scanning range. This is because the quality of the fan-beam reconstructed image is different from the quality of the cone-beam reconstructed image and the CT apparatus reconstructs a plurality of slice image in the scanning range using the cone-beam reconstruction and the fan-beam reconstruction. For example, when 6 images are reconstructed from projection data obtained from one scan, the prior art generates 6 images whose quality levels (noise levels) are a little different, because the 4 central images are reconstructed using the fan-beam reconstruction while the 2 peripheral images (one on each side of the 4 central images) are reconstructed using the cone-beam reconstruction. The difference in the image quality of the images produced from the common scan may cause confusion or extra efforts to a doctor to equalize the image quality. The difference of image quality is caused by the difference of the reconstruction method. In the fan-beam reconstruction, a tomographic image is backprojected along "single ray" of x-ray beams, because x-ray beams are assumed to intersect perpendicularly with the rotation center axis of the x-ray source. But, in the cone-beam reconstruction a tomographic image must be backprojected along "a plurality of" rays of x-ray beams. In the cone-beam reconstruction, it is assumed that the image comprises a plurality of voxels, and respective voxel is backprojected along a ray of x-ray beam. By not properly taking into account these differences in backprojection, image distortion can occur.

BRIEF SUMMARY OF THE INVENTION

Accordingly, it is an object of the present invention to devise a comprehensive cone-beam X-ray CT apparatus that can produce constant, high quality cone-beam and fan-beam images.

A computer tomography apparatus according to the present invention comprises an x-ray source configured to emit x-rays while rotating around an object to be examined; an x-ray detector configured to have a plurality of detection elements arranged along channel direction and slice-thickness direction and configured to detect x-rays passing through the object; a data acquisition device configured to acquire projection data about the object using the output of the x-ray detector; a setting device configured to select the number of slices to be processed; and a reconstructing device configured to selectably employ a first reconstruction method and a second reconstruction method. The reconstructing device is configured to determine the first reconstruction method or the second reconstruction method according to the number of slices selected and reconstruct an image based on the projection data using the selected reconstruction method. The x-rays are assumed to intersect perpendicularly with the rotation center axis of the x-ray source in the first reconstruction method. The second reconstruction method reconstructs the image using cone angle information of the x-rays.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, server to explain the principles of the invention.

DETAILED DESCRIPTION OF THE INVENTION

Figure 1:
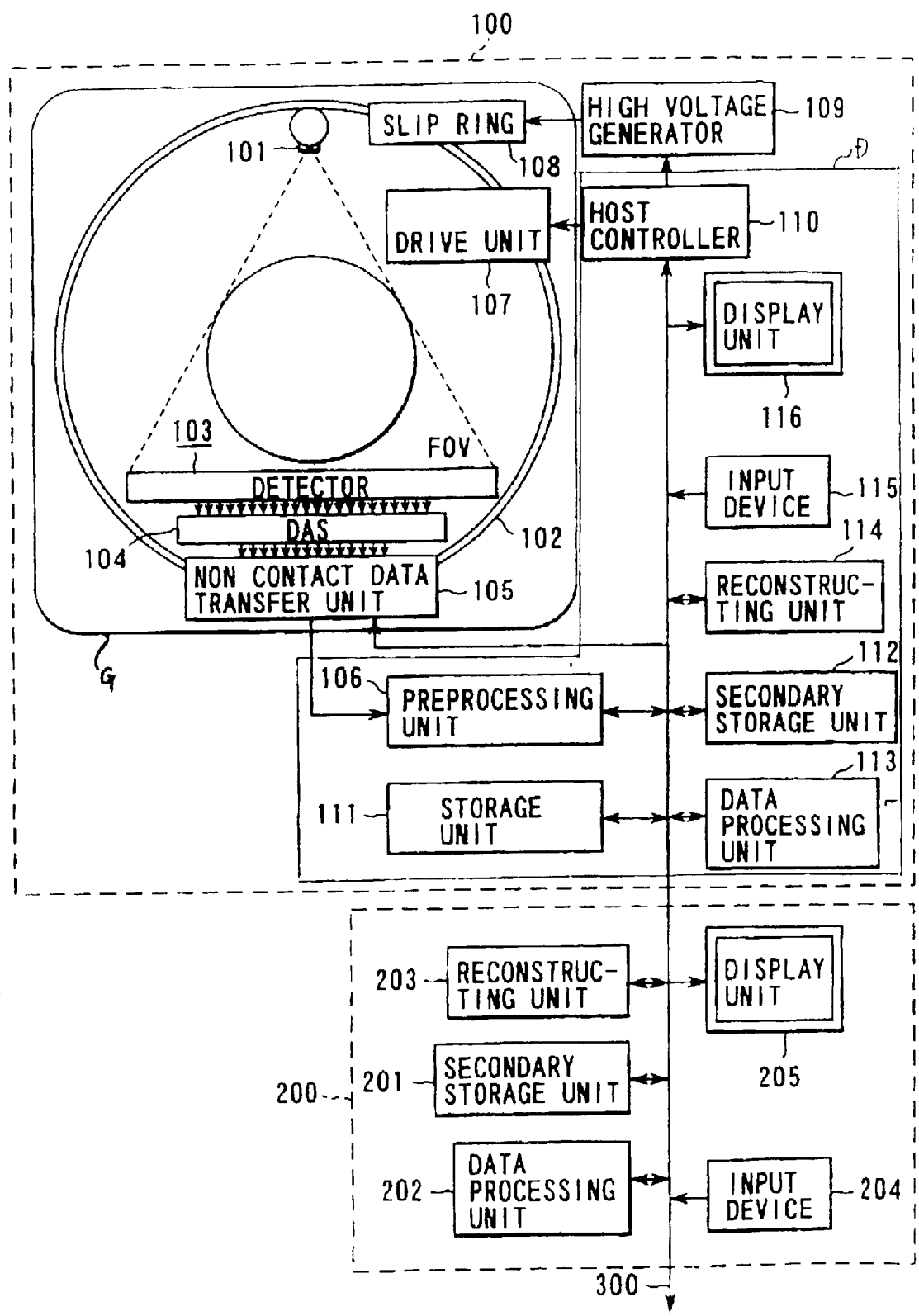
FIG. 1 is a block diagram schematically showing the configuration of an X-ray CT apparatus according to the first embodiment.

FIG. 1 shows a configuration of an X-ray CT apparatus according to the first embodiment. An x-ray CT apparatus 100 comprises a bed on which an object (for example, patient) lies down, a gantry for acquiring projection data of the object to be examined, and a data processing unit D for processing the projection data acquired by the gantry. The gantry includes a diagnosis opening portion in which the object is inserted for diagnosis. The data processing unit D controls the gantry. The data processing unit D controls to perform image reconstruction processing based on the acquired projection data, to display the reconstructed image, and perform other processing functions. The bed includes a tabletop, which can be driven to slide along the body axis of the object by a bed drive unit (not illustrated).

The gantry includes an x-ray tube 101, an radiation detector 103 mounted on a rotating ring 102 in a position opposing the X-ray tube 101, a group of switches 104a, a data acquisition system (DAS) 104b, a data transfer unit 105, a gantry drive unit 107, and a slip ring 108. The x-ray tube 101, the radiation detector 103, and the data acquisition system 104b are mounted on the rotation ring 102 and rotated around a center axis that is parallel to a body axis of the object by a gantry drive unit 107. The rotating ring 102 is driven by the gantry drive unit 107 at a speed as high as one second or less per rotation.

An X-ray tube 101 emits either a cone-shaped or a fan-shaped x-ray beam onto the object P placed in an effective field of view (FOV). Power (tube voltage and tube current) required for the radiation of X-rays is supplied from a high voltage generator 109 to the X-ray tube 101 through a slip ring 108. With this operation, the X-ray tube 101 generates a so-called X-ray cone beam or fan beam that diverges in two directions (a channel direction C) perpendicular to the body axis direction of the object and a slice direction A (i.e., a direction parallel to the rotation axis and perpendicular to the channel direction C).

A collimator (not illustrated) is equipped between the X-ray tube 101 in the gantry and the object to shape X-rays emitted from the X-ray focal point of the X-ray tube 101 so as to form the cone-beam X-ray or the fan-beam X-ray having a predetermined solid angle.

Radiation detector 103 detects X-rays passing through the object P. The radiation detector 103 has a plurality of detection elements configured to detect the x-rays passing through the object. The detection elements are arranged along a channel direction and a slice-thickness direction. The radiation detector 103 is constituted by a plurality of detector modules 1030. In one embodiment 38 detector modules are used. The plurality of detector elements are arrayed in the channel direction.

Figure 2:
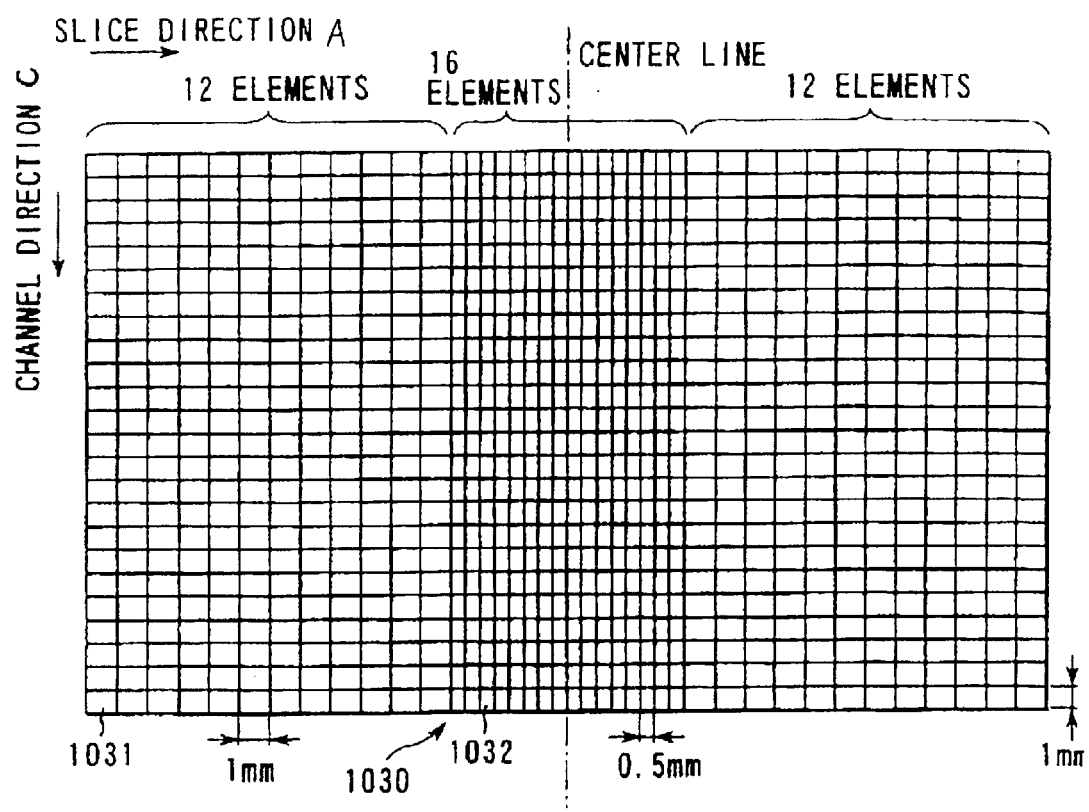
FIG. 2 shows the structure of one detector module of a radiation detector adapted to x-ray CT apparatus according to the first embodiment.

FIG. 2 is a developed view of one detector module 1030. The detector module 1030 includes a plurality of detector elements 1031, 1032. Each detector element has a scintillator and a photodiode chip (not illustrated). The plurality of detection elements 1031 and 1032 are arranged in the form of a matrix in two directions, i.e., the channel direction C and the slice direction A. The plurality of detector modules 1030 of the X-ray CT apparatus of this embodiment are arranged along an arc centered on the focal point of the X-ray tube 101. The modules 1030 may be arranged two-dimensionally.

As described above, the detector module 1030 includes a switching chip 104a and DAS chip 104b as well as the photodiode chip as an element of the plurality of detection elements 1031 and 1032. These detection elements 1031 and 1032, switching chip 104a, and DAS chip 104b are mounted on a rigid printed wiring board.

The detection element 1031 has a sensitivity range with a width of 1 mm in the slice-thickness direction and a width of 0.5 mm in the channel direction. The detection element 1032 has a sensitivity range with a width of 0.5 mm in the slice direction and a width of 0.5 mm in the channel direction.

In the following description, the width of sensitivity range of a photodiode is defined as a value converted on the rotation center axis of the X-ray tube. More specifically, a "photodiode having a sensitivity range width of 1 mm" is a photodiode having a sensitivity range width equivalent to 1 mm on the rotation center axis of the X-ray tube". In consideration of radial diffusion of X-rays, the actual sensitivity range width of a photodiode is slightly larger than 1 mm according to the ratio of the actual distance from the X-ray focal point and the sensitivity range of the photodiode to the actual distance from the X-ray focal point and the rotation center axis.

For example, 16 0.5-mm wide detection elements 1032 can be arranged in the slice direction A. The 16 detection elements 1032 arranged in the slice direction A will be referred to as a first detection element array group 1033. A plurality of arrays of 1-mm wide detection elements 1031 can be arranged in the slice direction A in number smaller than the number of arrays of detection elements 1032, e.g., 12, on each side of the first detection element array 1033. The 12 detection elements 1031 arranged in the channel direction C will be referred to as a second detection element array group 1034.

In this embodiment, the number (e.g., 16) of detection elements 1032 along the slice direction A is larger than the number (e.g., 12) of detection elements 1031 adjacent thereto and is smaller than the total number (e.g., 24) of detection elements 1031.

Namely, in the radiation detector 103 of this embodiment, 912 detection elements are arranged in the channel direction C (column direction), 40 detection elements are arranged in the slice direction A (row direction). The radiation detector 103 of this embodiment is an unequal size detector having 0.5-mm wide detection elements and 1-mm wide detection elements, but the equal size detector arranged same wide detection elements might be adapted. The size of the detection element is not limited 0.5 mm and 1 mm. For example, 1.25 mm and the other size might be adapted.

An enormous amount of data detected by M×N (M=24 (elements)×38=912, and N=40(=16 (elements)+2×12 (elements)) in this embodiment) channels per view will be referred to as "2D projection data" hereinafter) in the radiation detector 103 are temporarily collected in a data acquisition system (DAS) 104 which is formed as a chip. The detected data (projection data) are collectively transmitted to a data processing unit D (to be described later) through a non-contact transfer unit 105 to which optical communication is applied. The data transfer unit might not be the non-contact transfer unit 105 but a contact transfer unit such as a slip ring, etc.

The radiation detector 103 repeats detection about 1,000 times per rotation (about 1 sec). With this operation, an enormous amount of 2D projection data corresponding to M×N channels is generated 1,000 times per second (per rotation). To transmit such an enormous amount of 2D projection data, which is generated at high speed, without any delay, the data acquisition system 104b and non-contact transfer unit 105 are designed to perform ultra-high-speed processing. The X-ray transmission data detected by the detection elements are transmitted to the data acquisition system 104b by group of switches 104a. The number of data acquisition elements in the slice direction of the data acquisition system 104b is less than the number of the detection elements (channels) of the radiation detector 103. The number of detection elements is 40 rows. For example, the number of the data acquisition elements being switched on by the group of switches 104a 912 columns×8 rows or 912 columns×4 rows.

Figure 3:
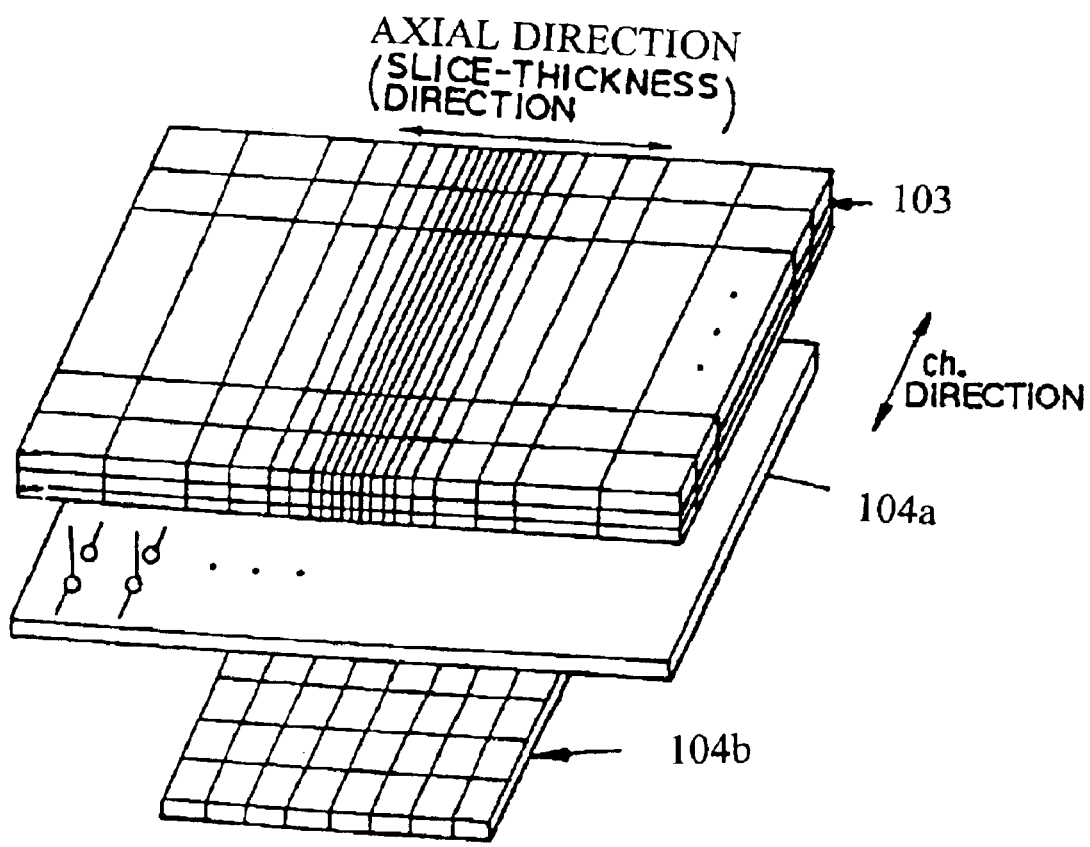
FIG. 3 is an oblique view schematically showing the radiation detector, a group of switches, and a data acquisition system.

FIG. 3 is an oblique view showing the structures of the two-dimensional detector 103, group of switches 104a, and DAS 104b of this embodiment. As shown in FIG. 3, the two-dimensional detector 103 has detection elements set in array, and the group of switches 104b have switching devices such as FETs mounted on, for example, a switching substrate. Each of the detection elements is made up of a scintillator layer, a light-transmitting resin layer, and a photodiode layer, thus X-rays reached the scintillator layer being converted to corresponding electric signals via photo signals. Alternatively, a semiconductor-detecting device directly converting X-rays to electric signals may be used. The data acquisition elements of the DAS 104b are laid out in the form of an array like the detecting elements of the two-dimensional detector 103.

The data acquisition elements of the DAS 104b acquire projection data of 8 slices or 4 slices of the object P by amplifying supplied X-ray transmission data items and converting them into digital signals. As mentioned later, in this embodiment, the number of the acquisition elements (the acquisition elements of 8 rows or 4 rows in the slice direction) may be determined according to a reconstruction method such as a fan-beam reconstruction, cone-beam reconstruction. The fan-beam reconstruction or the cone-beam reconstruction is selected when an examination plan is setup. In this embodiment, when the fan-beam reconstruction is performed (or 0.5 mm slice thickness×4 slices), 4 rows of the data acquisition elements (for example, 912 columns×4 rows) are used for acquiring the projection data, while 8 rows data acquisition elements (for example, 912 columns×8 rows) are used, the cone-beam reconstruction is performed (or 0.5 mm slice thickness×8 slices). The number of the acquisition elements in the slice direction may not be determined according to the reconstruction method. The number of the acquisition elements in the slice direction may be determined according to at least one of the number of slices (to be scanned or to be reconstructed), a slice width of slices defined by the number of the slices and slice thickness per image, and an opening width of the collimator in the slice direction.

In the data processing unit D, a host controller 110 serving as a main component, a preprocessing unit 106 for performing preprocessing such as data correction, a storage unit 111, a secondary storage unit 112, a data processing unit 113, a reconstructing unit 114, an input device 115, and a display unit 116 are connected to each other through a data/control bus 300. In addition, an external image processing unit 200 constituted by a secondary storage unit 201, data processing unit 202, reconstructing unit 203, input unit 204, and display unit 205 may be connected to the data processing unit D through this bus 300.

The preprocessing unit 106 performs preprocessing such as sensitivity correction and X-ray intensity correction to the projection data transferred through the non-contact transfer unit 105. The 360° 2D projection data, i.e., 1,000 sets of 2D projection data, having the sensitivity correction, X-ray intensity correction, and the like in the preprocessing unit 106 is sent to the reconstructing unit 114. The reconstructing unit 114 performs reconstruction based on the projection data using the at least one of the fan-beam reconstruction and the cone-beam reconstruction selected as mentioned above.

An image is reconstructed based on the projection data with the cone-beam reconstruction using a reconstruction method called the Feldkamp method. The cone-beam reconstruction is not limited to the Feldkamp method. The cone angle of the x-ray (x-ray path) may be used for the reconstruction such as the ASSR method. The ASSR method is the reconstruction method reconstructing from approximate of the x-ray path (ray), in which the approximate projection data of the x-ray path corresponding to a selected virtual plane is obtained from actually collected projection data in multi-helical CT. For example, the method can achieve to reconstruct a slanting tomograhic image by selecting the virtual plane along a helical orbit of an x-ray.

The Feldkamp reconstruction method is an approximate reconstruction method that has been improved on the basis of the fan beam convolution back-projection method to generate 3D profile data (to be referred to as volume data (a stereoscopic (3D) set of a plurality of voxel data)) of X-ray absorption coefficients by handling a target area that is wide in the slice direction A as a set of a plurality of voxels. That is, in the Feldkamp reconstruction method, data is regarded as fan projection data to perform convolution, and back-projection is performed along an oblique ray in accordance with an actual cone angle with respect to a rotation center axis (an axis of rotation of the x-ray tube 101).

In addition to the Feldkamp reconstruction method, at least one of following two correction processing may be performed when the cone-beam reconstruction is performed to make the error of the reconstruction can smaller.

A first correction processing corrects the beam path length of an x-ray beam passed through the object. Such a correction is desirable because the beam path length is aslant to a reconstruction plane (slice plane) and longer of the peripheral. Namely, the projection data acquired by the data acquisition system 104b is corrected according to a slice position in the slice direction where incidence of the x-ray beam is performed. For example, the projection data acquired from the end row of the detection elements is used for the reconstructing by small weighting compared with the projection data acquired from the central row.

A second correction processing corrects an offset between an actual, defined by a line connecting a focal spot and the center of the detection element, and a theoretical x-ray path, defined by an line connecting the focal spot of the x-ray and the center of a voxel to be reconstructed. Namely, the second correction processing creates projection data of theoretical x-ray path by calculating (for example, interpolating) projection data set of a plurality of x-ray paths that exist around the theoretical x-ray path, back-projects the created data along the theoretical x-ray path. A weighting of the projection data of the detector row to be calculated may be changed for each position of the focal spot (or each view).

By using the cone-beam reconstruction method, therefore, a detector which is wide in the slice direction can be effectively used.

Alternatively, a fan beam convolution back-projection method may be used. In the fan-beam reconstruction, a ray is assumed to be perpendicular to the axis (for example, body axis) of rotation of the x-ray tube 101 in back-projection, and the reconstructing unit 114 reconstructs an image based on the projection data according to the above supposition.

The reconstructed volume data is sent to the data processing unit 113 directly or after temporarily stored in the storage unit 111. In accordance with an instruction from the operator, the data is converted into widely used image data, i.e., a tomographic image of an arbitrary slice, a projection image from an arbitrary direction, and so-called pseudo 3D image data such as a 3D surface image of a specific organ upon rendering, and then the resultant images are displayed on the display unit 116.

The operator can select and set an arbitrary display mode among a tomographic image of an arbitrary slice, a projection image from an arbitrary direction, a 3D surface image, and the like in accordance with the purpose of examination/diagnosis. In this case, therefore, images in different forms can be generated from one volume data and displayed. In addition, the display modes include the mode of simultaneously displaying a plurality of types of images. This mode and the mode of displaying one image can be switched in accordance with a purpose.

The input device 2040 includes a keyboard, various switches, mouse, and the like, allows the operator to input and setup an examination plan on a setting screen (for example a display unit 116), and has a function for forming the examination plan. Parameters or conditions to be input or set for the examination plan includes a portion of the object to be examined such as a head, a sequence of processing steps from scanning to image recording, a scan condition for acquiring the projection data, a reconstruction condition for reconstructing one or a plurality of images, a display condition when the image is displayed, contents of voice message during the scanning is performed, and voice generating timing, etc.

The sequence from scanning to recording includes an auto-filming mode, etc. In the auto-filming mode a sequence of an image reconstruction such as the fan-beam reconstruction or the cone-beam reconstruction performed in parallel with a scan such as a helical scanning, and recording the reconstructed image using a window condition setup beforehand by a filming device is programmed and performed automatically.

An acquisition operation (scan operation) of the projection data relates to a plurality of parameters. An image generating operation relates to a plurality of parameters. The acquisition operation parameters (scan condition) include a scan type (conventional/helical), the number of slices to be scanned, a slice thickness to be scanned, a slice width defined by the number of slices multiplied by the slice thickness, a slice interval, FOV (Field Of View), a tilt angle of the gantry, a tube voltage, a tube current, a scan start position, a scan end position, a scan speed (the speed of rotating the x-ray tube 101 and the radiation detector 103), an amount of movement of the bed while the x-ray tube 101 and the radiation detector 103 are rotated, etc.

The image generation parameters (the reconstruction condition) include the image reconstruction method (fan-beam/cone-beam), the number of slices to be reconstructed, the slice thickness of slices to be reconstructed, a size of reconstruction area, and a matrix size of the reconstruction, etc. The display and recording parameters include window level, window width, and multi-planar (sagittal/coronal/oblique).

Acquisition operation parameters, the image generation parameters, and displaying and recording are registered beforehand so an operator can obtain a series of images by only selecting the examination plan.

With a plan form system, the operator can setup the examination plan (schedule) including the part to be examined, the flow from the scan to the record, the scan condition, the reconstruction condition, and the display condition. The host controller 110 thereby controls the gantry and the bed according to the setup schedule.

Figure 4:
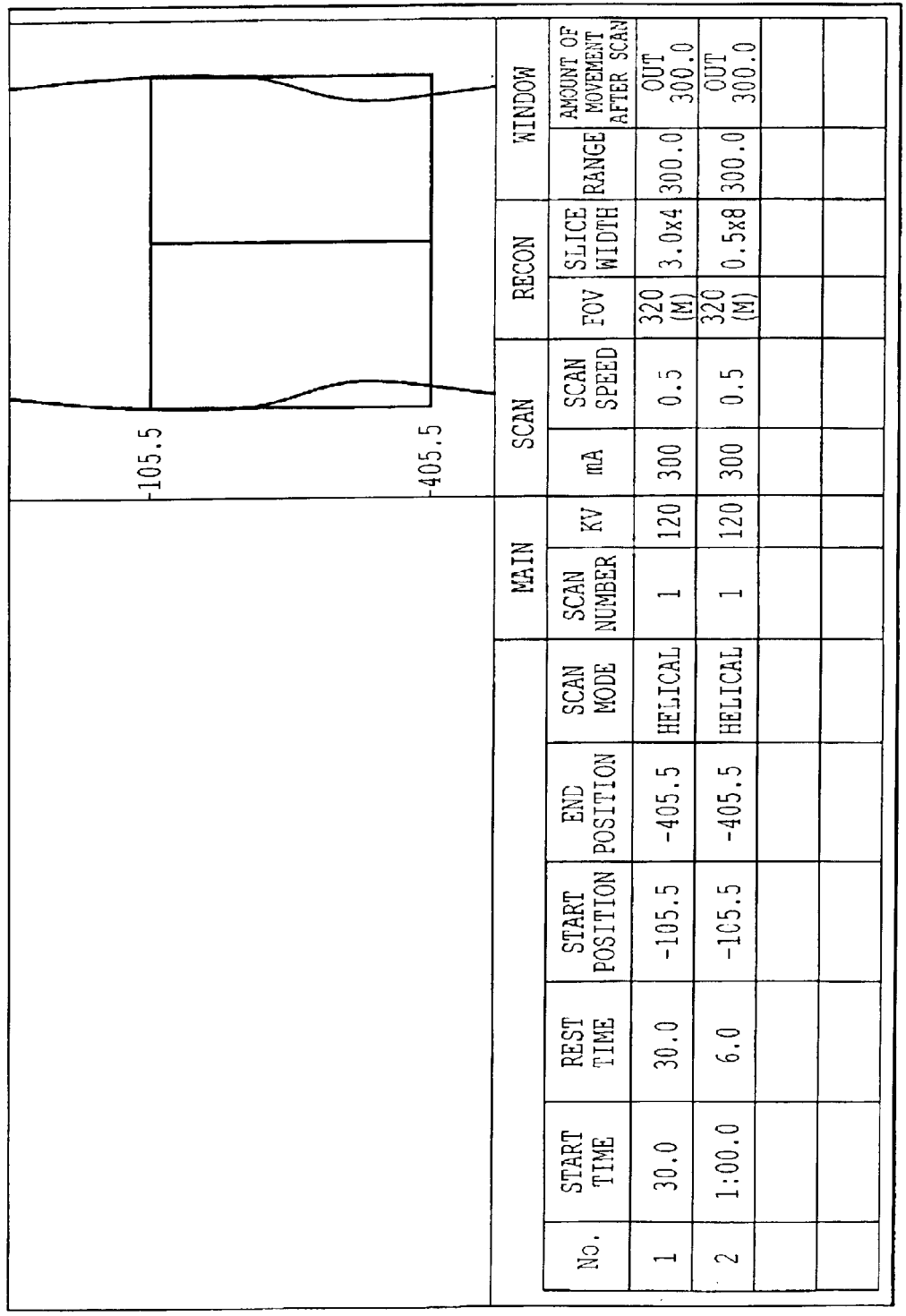
FIG. 4 shows a display example for an examination planning by an examination plan forming function.

FIG. 4 shows an example of an examination schedule setup screen. In this embodiment, a menu for setting up scanning parameters is shown as an example of the scan schedule screen in the examination schedule. In this embodiment, a scanogram (scout image) is displayed on the upper right portion of the screen. The scanogram is generated based on the projection data detected by the radiation detector 103 when the object (the tabletop) is moved along the body axis (slice direction). The lines for setting up a scan range are displayed on the scanogram. By moving the lines, the scan range is setup. A scan schedule table is displayed on a lower portion. In the scan schedule table, a plurality of examinations to be performed are perpendicularly arranged according to a predetermined order of the operation. The operator can modify the schedule by adding, copying, or deleting. Each rows of the examinations includes items such as a scan start time, a pause time between the examinations, a scan range (scan start position and scan end position), a scan mode (conventional scan or helical scan), the number of the examinations, an tube voltage and an tube current supplied to the x-ray tube 101 from the high voltage generator 109, a scan speed (the rotation speed), the size of the FOV, the slice width (the slice thickness×the number of slices to be scanned), the distance of movement of the table top between consecutive examinations, etc. If the operator changes a value of an item such as the scan range, a size and a position of the lines on the scanogram is changed. If one of the lines on the scanogram is moved, the item is changed according to the movement.

Instead of the slice width, the slice thickness multiplied by the number of slices to be scanned may be setup individually.

In a menu for setting reconstruction conditions, the reconstruction method (the fan-beam construction/the cone-beam reconstruction), the slice thickness×the number of slices to be constructed can be selected or input.

The scan and the reconstruction menus may be linked each other. When the operator changes the slice width in the scan sheet, at least one of the reconstruction methods and the slice width the reconstruction sheet may be changed automatically. When the operator changes the number of slices in the reconstruction sheet, at least one of the number of slices and the slice width in the scan sheet may be changed automatically.

Parameters in a common menu may be linked with each other. Thus, for example, when the operator changes the reconstruction method, the slice width in the reconstruction sheet may be changed automatically. When the operator changes the number of slices in the scan or reconstruction sheet, the slice width in the same sheet may be changed automatically.

The host controller 110 is equipped with a computer circuit having a CPU and connected to the high voltage generator 109. The host controller 110 is also connected to the bed drive unit (not shown), gantry drive unit 107, and radiation detector 103 in the gantry through a bus. In addition, the host controller 110, data processing unit 113, storage unit 111, reconstructing unit 114, display unit 116, and input device 115 are connected to each other through a bus, and can exchange image data and control data at high speed through the bus.

The host controller 110 executes a predetermined acquisition processing routine for X-ray transmission data (projection data). More specifically, the host controller 110 stores scanning conditions such as a slice width, input from the operator through the input device 115, in the internal memory, and drives the high voltage generator 109, bed drive unit, and gantry drive unit 107 while controlling the high voltage generator 109, the bed drive unit, the gantry drive unit 107, and the feed amount and speed of the bed (table top) in the body axis direction, the rotational speed and pitch of the gantry (the X-ray tube 101 and radiation detector 103), irradiation timing of X-rays, and the like. As a consequence, a desired imaging area of the object is irradiated with cone-beam x-rays or fan-beam x-rays from many directions, and the transmission X-rays transmitted through the imaging area of the object can be detected as X-ray transmission data through the respective detection elements of the radiation detector 103.

The host controller 110 controls ON/OFF of the switching elements 104a between the radiation detector 103 and the data acquisition system 104b on the basis of at least one of the reconstruction method (the fan-beam reconstruction/the cone-beam reconstruction) and the slice width (or the number of slices) setup by the input device 115. The host controller 110 controls the connecting status between the respective detection elements (photodiodes) of the radiation detector 103 and the DAS 104b. As a result, the host controller 110 controls the number of the data acquisition elements for acquiring the projection data in the slice direction according to the reconstruction method to combine the x-ray transmission data detected by the respective detection elements in a predetermined unit. For example, 4 rows of the acquisition elements in the slice direction are used when the fan-beam reconstruction is selected, 8 rows of the acquisition elements in the slice direction are used when the cone-beam reconstruction is selected. The host controller 110 sends to the DAS 104b the resultant data as X-ray transmission data of a plurality of slices corresponding to the scanning conditions and the reconstruction conditions, and executes predetermined processing.

Alternatively, host controller 110 may be configured to determine the reconstruction method of the reconstructing unit 114 according to the number of slices or the slice width setup by the input device 115. For example, the reconstructing unit 114 reconstructs 4 tomographic images based on the projection data using the fan-beam reconstruction when the number of the slices is set as 4 (or 0.5 mm×4 slices), and reconstructs 8 tomographic images based on the projection data using the cone-beam reconstruction when the number of the slices is set as 8 (or 0.5 mm×8 slices)

The function/effect of the X-ray CT apparatus will be described below. This example is a case where the helical scan (this is also called spiral scan.) is selected as the scan mode. The helical scan acquires projection data by the object or the gantry while rotating an x-ray source. In the helical scan, during irradiation of x-rays, the position that has been scanned changes continuously according to the rotation angle of the x-ray source. In other words, the position of scan plane to the object is changed continuously. The transmitted data acquired by the helical scan is processed according to the following methods and images of a plurality of slice plane are reconstructed.

First, an operator acquires a scanogram. The scanogram is generated based on projection data detected by the radiation detector 103 when an object is moved along the slice direction.

Next, the operator setups a scanning portion, for example, abdomen of the object. The operator setups the examination plan such as the processing sequence from the scan to the recording, the scan condition, the reconstruction condition, and the display condition by support of the plan form system. The screen as shown in FIG. 4 is displayed on the setup screen of the input device 115. Then, An operator clicks the scan menu and setups scanning conditions. Not only scan range, the scan start position, the scan end position, FOV, etc but also the slice width as the scanning condition are setup.

If the slice width is setup as "the slice thickness is 0.5 mm and the number of slices is 4 (0.5 mm×4 slices)", the host controller 110 sets the reconstructing method in the reconstructing unit as the fan-beam reconstruction. If the slice width is setups as "the slice thickness is 0.5 mm and the number of slices is 8 (0.5 mm×8 slices)", the host controller 110 sets the reconstructing method in the reconstructing unit as the cone-beam reconstruction.

When such the examination plan is setup, a plurality of parameters about the data acquisition, the image generation, and the image display related with the examination plan are transferred to the host controller 110.

If the operator instructs to start the examination, the tabletop is moved till just before a scanning start position (a run-up position of the helical scan), and the rotating ring 102 rotates so that a scan speed setup in the examination plan is reached. When the speed of the rotating ring 102 reaches the setup speed (0.5 second per rotation, in FIG. 4), the tube voltage and the tube current setup in the examination plan are supplied from the high voltage generator 109 to the x-ray tube 101, and the x-rays are emitted from the x-ray tube 101 while sliding the tabletop in the body axis (slice direction). Until this time, the opening width of the collimator is adjusted so that the projection data of the setup slice width is acquired. Thus, the helical scan is performed by moving the object in the slice direction while the x-ray tube 101 is rotated around the object.

The X-rays passed through the object are converted into 2D projection data, which is an analog electrical signal, by the radiation detector 103. This data is converted into 2D projection data, which is a digital electrical signal, by the data acquisition system 104. The data is then sent to the preprocessing unit 106, which performs various types of correction, through the non-contact transfer unit 105 to be subjected to sensitivity correction and the like.

The number of the data acquisition elements (DAS 104*b*) for acquiring the projection data and the connecting status between the radiation detector 103 and the DAS 104*b* is switched according to the selected reconstruction method (the fan-beam reconstruction or the cone-beam reconstruction).

When the fan-beam reconstruction is selected, 912 columns×4 rows of the acquisition elements in the slice direction are used for the acquisition (amplification processing, A/D conversion, etc), when the cone-beam reconstruction is selected, 912 columns×8 rows of the acquisition elements in the slice direction are used for the acquisition.

In this embodiment, when the fan-beam reconstruction is setup, the tomographic images can be obtained by the mode of 0.5 mm×4 slice, 1.0 mm×4 slice, 2.0 mm×4 slice, 3.0 mm×4 slice, or 4.0 mm×4 slice.

The x-ray CT apparatus of this embodiment can theoretically obtain 4 tomographic images of a slice thickness exceeding 4.0 mm (for example, 8.0 mm×4 slice), however it would be desirable to have a restriction of the maximum detection range in the slice direction because the cone angle would be too large to reconstruct an image with the fan-beam reconstruction method. The maximum slice thickness may not be limited to 4 mm, for example, 3 mm.

In scanning 4×0.5 mm slice width, the projection data for reconstructing 4 tomographic images of 0.5 mm slice thickness can be acquired by individually reading out electrical signals from 4 central rows of the 0.5 mm width detection elements 1031. Then, each detection elements 1031 are individually connected to 4 rows (in 8 rows) of the data acquisition elements of the DAS 104*b* by the group of switches 104*a*. The another 4 of the rows data acquisition elements are not used, the output of other rows of the detection elements except the 4 central rows are connected to GND by the group of switches 104*a*.

In scanning 4×1.0 mm slice width, 8 central rows of the 0.5 mm width detection elements 1031 are connected to the DAS 104*b* so that pairs of adjacent 0.5 mm width detection elements 1031 are connected the data acquisition elements of the same rows in the DAS 104*b* by the group of switches 104*a*. Thus, 8 rows of the detection elements 1031 are connected to 4 rows of DAS 104*b* using the group of switches 104*a*. That is, the projection data for reconstructing 4 tomographic images of 1.0 mm slice thickness can be determined by adding the electrical signals of the detection elements 1031 of same channels (the electrical signals are simultaneously read out from pairs of adjacent 0.5-mm wide detection elements 1031 so as to handle each pair as a single element). The other 4 rows of data acquisition elements are not used, the output of other rows of the detection elements except the central rows are connected to GND by the group of switches 104*a*.

When 4×2.0 mm slice width, 4×3.0 mm slice width, or 4×4.0 mm slice width is used, the same addition processing as 4×1.0 mm slice width is used.

On the other hand, when the cone-beam reconstruction is selected, the addition processing which the connected state between the radiation detector 103 and DAS 104*b* is switched according to the slice width is performed as the selected fan-beam reconstruction case. But it differs greatly that the cone-beam reconstruction mode uses more numbers of the acquisition elements (in this embodiment, DAS 104*b* of all 8 rows) than the fan-beam reconstruction mode. With such an operation, when the cone-beam reconstruction is setup, the tomographic images can be obtained by the mode of 0.5 mm×8 slice, 1.0 mm×8 slice, 2.0 mm×8 slice, 3.0 mm×8 slice, or 4.0 mm×8 slice.

In this embodiment, when the fan-beam reconstruction is selected, the projection data is acquired by the data acquisition elements (DAS 104*b*) of 4 rows. The number of rows of DAS 104*b* is not limited to 4 rows. The number of rows may be 1 or, 2, etc. When the cone-beam reconstruction is selected, the projection data is acquired by the data acquisition elements (DAS 104*b*) of 8 rows. The number of rows of DAS 104*a* is not limited to 8 rows, if the number of DAS 104*b* in the case of selecting the cone-beam reconstruction is larger than the number of DAS 104*b* in the case of the fan-beam reconstruction. The number of rows in the case of the cone-beam reconstruction may be 16, 32, 64 rows etc.

For example, if the DAS 104*b* of 2 rows are selected in the case of the fan-beam reconstruction, the DAS 104*b* of 4 rows is selected in the case of the cone-beam reconstruction.

The 360° 2D projection data, i.e., 1,000 sets of 2D projection data, having sensitivity correction, X-ray intensity correction, and the like in the preprocessing unit 106 is sent to the storage unit 111. The data processing unit 113 performs the following interpolation processing and correction processing to the projection data.

When the fan-beam reconstruction is selected, the reconstructing unit 114 reconstructs an image based on the projection data supposing the x-rays intersect perpendicularly with the axis of the rotation of the x-ray tube 101. The data processing unit 113 performs helical interpolation using the projection data before the image reconstruction. The helical interpolation is to obtain projection data for reconstructing an image (spanning of 360 degree or spanning of 180 degree plus fan angle) by performing linear interpolation using two projection data of same views near a target slice plane.

In another embodiment, the helical interpolation is improved. When the fan-beam reconstruction is selected, the data processing unit 113 performs a filter-like interpolation with re-sampling is characterized by determining a plurality of slicing locations adjacent to the target slicing location which are spaced at equal intervals of a small distance, producing a group of interpolated data (re-sampled data) between data sampled at the slicing locations, and subjecting the interpolated data (re-sampled data) to the weighted addition or filtering to have a data at the target slicing location. The reconstructing unit 114 reconstructs an image based the produced data using the fan-beam reconstruction.

On the other hand, when the cone-beam reconstruction is selected, the data processing unit 113 does not perform the helical interpolation like the fan-beam reconstruction. The data processing unit 113 performs the first correction processing and the second correction processing. By the first correction processing, the projection data for reconstructing the image is corrected according to the path of length of the x-ray beam, wherein the length is different according to the detection position of the cone-beam x-rays in the body axis direction. By the second correction processing, the projection data is corrected according the difference between the actual x-ray path to be sampled and the theoretical x-ray path to be calculated. The reconstructing unit 114 reconstructs the image by back-projecting the corrected projection data along the x-ray path to be calculated.

The display unit 116 displays the reconstructed image generated by the reconstructing unit 114. According to setup the examination plan, the reconstructed data may be stored in the storage unit 111. After that, in accordance with an instruction from the operator, the data is converted into a well-known type of image data, i.e., a tomographic image of an arbitrary slice, a projection image from an arbitrary direction, and so-called pseudo 3D image data such as a 3D surface image of a specific organ upon rendering, and then the resultant images are displayed on the display unit 116.

According to the above arrangement, the following effects can be obtained.

As mentioned above, the reconstructing device of this embodiment has the fan-beam reconstruction and the cone-beam reconstruction, and the operator can select one of the reconstruction methods. The operator may select the fan-beam reconstruction when he performs an image diagnosis in a short time such as a screening examination and select the cone-beam reconstruction when he performs a careful image diagnosis with a high image quality.

The x-ray CT apparatus of this embodiment switches the number of DAS for acquiring the projection data according the selected reconstruction method (fan-beam reconstruction or cone-beam reconstruction). Therefore, it is effective in respect of the mounting space of DAS and cost.

The x-ray CT apparatus of this embodiment determines the reconstruction method (fan-beam reconstruction or cone-beam reconstruction) according to the number of slices to be scanned or to be reconstructed. Therefore, the operator does not need to take the relation between the number of slices and the reconstruction method into consideration, and the operator's burden is decreased.

The tomographic images of setup numbers are reconstructed using the same reconstruction method, the qualities of the images are substantially equal. Therefore, doctors can diagnose without considering the difference of qualities of images, and it can mitigate doctors' burden.

In this embodiment, the number of DAS and the connection status between radiation detector and the DAS are switched according to the reconstruction method setup in the examination plan. Therefore, the operators may not perform the operation for switching the number of DAS, and it can raise operability.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

For example, in the above embodiment, the number of DAS for acquiring the projection data is selected from 8 rows or 4 rows in the body axis direction according to the reconstruction method setup in the examination plan. The number of DAS (for example, 8 rows) may not be switched regardless of the selected reconstruction method. In this case, the number of slices such as 4 slices, 8 slices may be selected by the reconstruction sheet in the examination plan. By this, when the operator does not select the number of slices to be scanned in the examination plan, both 4 slices (tomographic images) and 8 slices are reconstructed. Thus, time can be saved.

In the above embodiment, the number of the data acquisition elements in the slice direction equals the number of slices to be scanned or reconstructed in order to obtain the tomographic images of the max number of slices setup by examination plan, however, the number of the data acquisition elements (for example, 16 rows) may be larger than the max number of slices. In this case, the electrical signals from not only the data acquisition elements for obtaining images of the max number but also the other data acquisition elements should be read out, they should be transferred to the data processing unit D side by data transfer unit 105. By this, upgrade about the increase in the number of the maximum slices (for example, 16 slices) can be easily carried out only by changing the software for a user interface, switching the data acquisition elements, and the other data processing.

In the above embodiment, since two kinds of images, the cone-beam reconstructed images and the fan-beam reconstructed images, are obtained it might be expected that the quality level of images are a little difference due to the difference of the reconstruction method, and a doctor might have a sense of incongruity. In order to solve the problem, a correction processing may be performed so that at least one of image SD, contrast, density of the cone-beam reconstructed images equals that of the fan-beam reconstructed images, when the images are obtained using the cone-beam reconstruction. Especially, the correction processing may be performed during a convolution of the cone-beam reconstruction, since a fine control is easier at this stage. Alternatively, the correction processing may be performed in the stage of preprocessing or after reconstructing. The correction processing may be performed to the fan-beam reconstructed images, and to both of the cone-beam reconstructed images and the fan-beam reconstructed images.

When the projection data set of 2.0 mm×8 slice (by using data acquisition elements of 8 rows) are acquired, tomographic images are generated. In the above embodiment, 4.0 mm×4 slice tomographic images can be generated. However, such restriction are not necessary ages of 4.0 mm×4 slice may be reconstructed based on projection data added after DAS using fan-beam reconstruction. 2.0 mm×8 slice scan and 4.0 mm×8 slice scan are detected by same detection elements of the radiation detector. By using this situation, when the operator selects 4 as the number of slices to be reconstructed (fan-beam reconstruction), the projection data sets are acquired by the data acquisition elements of 8 rows (not 4 rows), the fan-beam reconstruction or the cone-beam reconstruction is performed after addition of the projection acquired by DAS. By this, lines for readout the electrical signals and the connection patterns of switches for all data acquisition pattern (between the radiation detector and the DAS) may not be necessary. As long as the images are not badly affected, the lines and the connection patterns need not be common to the fan-beam reconstruction and the cone-beam reconstruction, and the addition processing may be performed after acquiring the projection data by the DAS.

In the above embodiment, data processing such as reconstruction and slice conversion and display operation are performed within an X-ray CT apparatus 100 (such a form of operation is general). However, instead of this form of operation these data processes and the like may be executed in the present invention by the external image processing unit 200 in FIG. 1. When this external image processing unit 200 is to be used, the data sent from the X-ray CT apparatus 100 to the image processing unit 200 does not impair the effects of the above embodiment in any state, e.g., before reconstruction, after reconstruction, or immediately before display after data processing.

Moreover, the above embodiment can be variously modified. For example, in the above embodiment, although the example of helical scanning was explained, it may be applied to conventional scanning.

Also, although the example of a rotate/rotate type in which the x-ray tube and the radiation detector rotate together around the object to be examined was explained, the present invention may be applied to a stationary/rotate type in which many detection elements arrayed in the form of a ring, and only an X-ray tube rotates around an object.

In the above embodiment, although the example which projection data corresponding to one rotation around the object, i.e., about 360 degree is required to reconstruct one tomographic image was explained, the present invention may be applied half scan method which projection data corresponding to spanning of 180 degree plus fan angle is required. The present invention can be applied to either scan (reconstruction).

The mainstream mechanisms for converting incident x-rays into charge are an indirect conversion type in which x-rays are converted into light by a phosphor such as a scintillator, and the light is converted into charge by photoelectric conversion elements such as photodiodes, and a direction conversion type using a photoconductive phenomenon in which electron-hole pairs are generated in a semiconductor by specific x-rays and move to electrodes. The x-ray detection elements may be used either scheme.

Also, although the example of one tube type x-ray CT apparatus was explained, the present invention may be applied to a plurality of tube type x-ray CT apparatus which a plurality of pairs of an x-ray tube and radiation detector are mounted on a rotating ring.

In the above embodiment, a fan-beam reconstruction or a cone-beam reconstruction is determined according to at least one of the number of slices to be scanned and scan slice width defined by the number of the scan slices and slice thickness of the slice to be scanned. The reconstruction method may be determined according to one of the number of slices to be reconstructed (the number of image slices) and reconstruction slice width defined by the number of the reconstructed slices and slice thickness of slice to be reconstructed. Moreover, the fan-beam reconstruction or the cone-beam reconstruction may be determined according an opening width in body axis direction of a collimator determined from the setup number of slices or the setup slice width. The x-ray CT apparatus may be comprised so that an operator can setup an opening width of a collimator, the image reconstruction method may be determined according to the collimator width.

What is claimed is:

1. A computer tomography apparatus, comprising:
   an x-ray source configured to emit x-rays while rotating around an object to be examined;
   an x-ray detector having x-ray detection elements arranged in a plurality of rows along a slice-thickness direction, at least one row having a number of x-ray detection elements configured to detect x-rays passed through the object and produce projection data of the object;
   a data acquisition device configured to acquire the projection data;
   a reconstruction device configured to reconstruct an image using one of a fan-beam reconstruction method and a cone-beam reconstruction method;
   a setting device configured to select a number of slices to be analyzed; and
   a reconstructing device selector configured to select, in correspondence to the number of slices selected, said one of a fan-beam reconstruction method and a cone-beam reconstruction method.

2. The apparatus of claim 1, wherein the reconstruction unit comprises:
   a reconstruction back-projection device, wherein
   the reconstruction back-projection device is configured to back-project projection data along a ray corresponding to x-ray cone-angle information of the cone-beam reconstruction method.

3. The apparatus of claim 2, wherein the reconstruction unit, when using the cone-beam reconstruction method, is configured to reconstruct a number of images larger than a number of images reconstructed used in the fan-beam reconstruction method.

4. The apparatus of claim 2, further comprising:
   a correction device configured to correct at least one of a cone beam reconstructed image and a fan-beam reconstructed image so that a post-correction cone beam reconstructed image and a post-correction fan-beam reconstructed image have substantially equal image quality.

5. The apparatus of claim 4, wherein said correction device comprises:
   a cone-beam reconstructed data correction device configured to correct cone-beam projection data.

6. The apparatus of claim 1, wherein the reconstruction devices comprises:
   an ASSR device configured to back-project the projection data along a selected slanting plane having a predetermined correspondence to a cone angle.

7. The apparatus of claim 1, wherein said data acquisition device comprises:
   a plurality of data acquisition elements arranged along a channel direction and the slice-thickness direction and configured to acquire the projection data; and
   a switching device configured to select a predetermined number of the data acquisition elements arranged along the slice-thickness direction according to the predetermined number of slices selected by the setting device.

8. The apparatus of claim 7, wherein the plurality of data acquisition elements comprises:

a number of data acquisition elements arranged in the slice-thickness direction less than the number of the x-ray detection elements in one of the plurality of rows arranged in the slice-thickness direction.

9. The apparatus of claim 7, wherein the plurality of data acquisition elements comprises:

a number of the data acquisition elements arranged in the slice-thickness direction larger than a maximum predetermined number of slices selectable by the setting device.

10. A computer tomography apparatus, comprising:

an x-ray source configured to emit x-rays while rotating around an object to be examined;

an x-ray detector having detection elements arranged in a plurality of rows along a slice-thickness direction, at least one row having a plurality of detection elements configured to detect x-rays passed through the object and produce projection data of the object;

a data acquisition device configured to acquire the projection data;

a reconstruction device configured to reconstruct an image from the acquired projection data assuming the x-rays intersect perpendicularly with an axis of rotation of the x-ray source so as to produce a fan-beam reconstructed image, said reconstruction device further configured to reconstruct an image from the acquired projection data using x-ray cone angle information so as to produce a cone-beam reconstructed image;

a setting device configured to select a slice width to be analyzed; and a reconstructing device selector configured to select, in correspondence to the slice width selected, whether the reconstruction device produces a fan-beam reconstructed image or produces a cone-beam reconstructed image.

11. A computer tomography apparatus, comprising:

an x-ray source configured to emit x-rays while rotating around an object to be examined;

a collimator having a aperture width selectable in the slice-thickness direction and configured to shape the emitted x-rays;

an x-ray detector having detection elements arranged in a plurality of rows along a slice-thickness direction, at least one row having a plurality of detection elements configured to detect x-rays passed through the object and produce projection data of the object;

a data acquisition device configured to acquire the projection data;

a reconstruction device configured to reconstruct an image from the acquired projection data assuming the x-rays intersect perpendicularly with an axis of rotation of the x-ray source so as to produce a fan-beam reconstructed image, said reconstruction device further configured to reconstruct an image from the acquired projection data using x-ray cone angle information so as to produce a cone-beam reconstructed image; and a reconstructing device selector configured to select, in correspondence to the selected aperture width of said collimator, whether the reconstruction device produces a fan-beam reconstructed image or produces a cone-beam reconstructed image.

12. A computer tomography apparatus, comprising:

an x-ray source configured to emit x-rays while rotating around an object to be examined;

an x-ray detector having detection elements arranged in a plurality of rows along a slice-thickness direction, at least one row having a plurality of detection elements configured to detect x-rays passed through the object and produce projection data of the object;

a switchable data acquisition device having a plurality of data acquisition elements arranged along a channel direction and the slice-thickness direction and configured to acquire the projection data;

a reconstruction device configured to reconstruct an image from the acquired projection data assuming the x-rays intersect perpendicularly with an axis of rotation of the x-ray source so as to produce a fan-beam reconstructed image, said reconstruction device further configured to reconstruct an image from the acquired projection data using x-ray cone angle information so as to produce a cone-beam reconstructed image;

a reconstruction device selector configured to select whether the reconstruction device produces a fan-beam reconstructed image or produces a cone-beam reconstructed image; and a data acquisition element switch configured to select a predetermined number of data acquisition elements from said plurality of data acquisition elements in correspondence with the selected reconstructed image.

13. The apparatus of claim 12, wherein the reconstruction devices comprises:

a reconstruction back-projection device configured to back-project the projection data along a ray corresponding to x-ray cone-angle information.

14. The apparatus of claim 12, wherein said data acquisition element switch comprises:

a group of switches connecting said x-ray detector and said data acquisition device and configured to select a first predetermined number of data acquisition elements along the slice-thickness direction when the fan-beam image is selected, and a second predetermined number of data acquisition elements along the slice-thickness direction when the cone-beam image is selected, wherein said second predetermined number is larger than said first predetermined number.

15. The apparatus of claim 1, wherein the number of slices to be analyzed comprises:

at least one of a number of slices to be scanned and a number of slices to be reconstructed.

* * * * *